US009091467B2

(12) United States Patent
Shreve et al.

(10) Patent No.: US 9,091,467 B2
(45) Date of Patent: Jul. 28, 2015

(54) THERMAL CONTROL OF THERMAL CHAMBER IN HIGH-PERFORMANCE LIQUID CHROMATOGRAPHY SYSTEMS

(75) Inventors: Joshua A. Shreve, Franklin, MA (US); Steven J. Ciavarini, Natick, MA (US)

(73) Assignee: Waters Technologies Corporation, Milford, MA (US)

( * ) Notice: Subject to any disclaimer, the term of this patent is extended or adjusted under 35 U.S.C. 154(b) by 388 days.

(21) Appl. No.: 13/519,776

(22) PCT Filed: Jan. 11, 2011

(86) PCT No.: PCT/US2011/020725
§ 371 (c)(1),
(2), (4) Date: Jun. 28, 2012

(87) PCT Pub. No.: WO2011/085337
PCT Pub. Date: Jul. 14, 2011

(65) Prior Publication Data
US 2012/0285872 A1    Nov. 15, 2012

Related U.S. Application Data

(60) Provisional application No. 61/293,827, filed on Jan. 11, 2010.

(51) Int. Cl.
*F25B 21/02*    (2006.01)
*G01N 30/24*    (2006.01)
*G01N 30/30*    (2006.01)

(52) U.S. Cl.
CPC ............... *F25B 21/02* (2013.01); *G01N 30/24* (2013.01); *G01N 30/30* (2013.01); *F25B 2321/0212* (2013.01); *F25B 2321/0251* (2013.01); *F25B 2700/2103* (2013.01); *F25D 2700/02* (2013.01); *F25D 2700/12* (2013.01); *F25D 2700/123* (2013.01); *G01N 2030/303* (2013.01)

(58) Field of Classification Search
CPC ............. F25B 21/02; F25B 2321/0251; F25B 2321/0212; F25B 2321/02; F25B 21/04; F25B 2700/15; F25B 2700/21; F25B 2700/2103; F25B 2700/2104; F25B 2700/2107; F25B 2700/2108; G01N 30/24; G01N 2030/303; G01N 30/30; F25D 2700/123; F25D 2700/12; F25D 2700/02; H01L 23/38; H01L 35/00; H01L 35/28; H01L 35/30; F24F 5/0042; F24F 11/0006; B01D 15/10
See application file for complete search history.

(56) References Cited

U.S. PATENT DOCUMENTS 4,328,676 A * 5/1982 Reed .............................. 62/3.62
5,290,340 A   3/1994 Gatten et al.
(Continued)

OTHER PUBLICATIONS
International Search Report and Written Opinion for counterpart international application No. PCT/US2011/020725 dated Mar. 11, 2011; 10 pages.

*Primary Examiner* — Lucas Stelling
*Assistant Examiner* — Rohit K Dewan
(74) *Attorney, Agent, or Firm* — Schmeiser, Olsen & Watts LLP; Michael A. Rodriguez

(57) ABSTRACT

A sample manager of a liquid chromatography system implements a thermal system that uses a dual-loop feedback control system to control temperature within a thermal chamber. The sample manager includes an external heatsink disposed externally to the thermal chamber, an internal heatsink disposed within the thermal chamber, and one or more thermoelectric devices thermally coupled to the external and internal heatsinks to transfer heat therebetween in response to a pulse-width modulated power signal. A first temperature sensor disposed within the thermal chamber continuously measures a chamber temperature. A second temperature sensor coupled to the internal heatsink within the thermal chamber continuously measures temperature at the internal heatsink. A feedback control system controls a duty cycle of the pulse-width modulated power signal in response to a target chamber temperature and real-time temperature measurements produced by the first and second temperature sensors.

17 Claims, 6 Drawing Sheets

(56) References Cited

U.S. PATENT DOCUMENTS

| | | | |
|---|---|---|---|
| 5,655,375 A * | 8/1997 | Ju | 62/3.6 |
| 6,052,998 A * | 4/2000 | Dage et al. | 62/89 |
| 6,632,015 B2 | 10/2003 | Nagasawa | |
| 2005/0011199 A1* | 1/2005 | Grisham et al. | 62/3.7 |
| 2005/0039465 A1* | 2/2005 | Welch | 62/3.7 |
| 2005/0174737 A1* | 8/2005 | Meir | 361/697 |
| 2009/0062965 A1 | 3/2009 | Alhilo | |
| 2010/0307168 A1* | 12/2010 | Kohl et al. | 62/3.6 |

* cited by examiner

THERMAL CONTROL OF THERMAL CHAMBER IN HIGH-PERFORMANCE LIQUID CHROMATOGRAPHY SYSTEMS

RELATED APPLICATION

This application claims priority to and the benefit of U.S. provisional application Ser. No. 61/293,827, filed on Jan. 11, 2010, the entirety of which application is incorporated by reference herein.

FIELD OF THE INVENTION

The invention relates generally to chromatography systems. More specifically, the invention relates to controlling temperature in a thermal chamber of a high-performance liquid chromatography system.

BACKGROUND

Chromatography is a set of techniques for separating a mixture into its constituents. For instance, in a liquid chromatography application, a pump takes in and delivers a mixture of liquid solvents to a sample manager, where an injected sample awaits its arrival. In an isocratic chromatography application, the composition of the liquid solvents remains unchanged, whereas in a gradient chromatography application, the solvent composition varies over time. The mobile phase, comprised of a sample dissolved in a mixture of solvents, passes to a column, referred to as the stationary phase. By passing the mixture through the column, the various components in the sample separate from each other at different rates and thus elute from the column at different times. A detector receives the elution from the column and produces an output from which the identity and quantity of the analytes may be determined.

During many chromatographic runs, the sample manager may maintain the sample at a low, near-freezing temperature. Critical to the reliability of the outcome of a chromatographic result is the ability to maintain the temperature consistently within the sample chamber (also called a thermal chamber). Because there are temperature differences between the cooling engine and the thermal chamber, the cooling engine needs to run colder than the desired chamber temperature. In addition, invariably there is moisture within the thermal chamber. This moisture condenses on the cooling engine, and will freeze if the cooling engine is at or below the freezing point. Icing of the cooling engine degrades the ability to control chamber temperature, which can have deleterious effects on the results of the chromatographic run.

SUMMARY

In one aspect, the invention features an apparatus comprising a thermal chamber, an external heatsink disposed externally to the thermal chamber, an internal heatsink disposed within the thermal chamber, and one or more thermoelectric devices thermally coupled to the external and internal heatsinks to transfer heat therebetween in response to a pulse-width modulated power signal. A first temperature sensor disposed within the thermal chamber continuously measures a chamber temperature. A second temperature sensor coupled to the internal heatsink within the thermal chamber continuously measures temperature at the internal heatsink. A feedback control system controls a duty cycle of the pulse-width modulated power signal in response to a target chamber temperature and real-time temperature measurements produced by the first and second temperature sensors.

In another aspect, the invention features a method for controlling temperature in a thermal chamber of a liquid chromatography system. Heat is transferred between an internal heatsink disposed within the thermal chamber and an external heatsink disposed externally to the thermal chamber using one or more thermoelectric devices thermally coupled between the heatsinks. Temperature is measured in real time at a first location in the thermal chamber and at a second location on the internal heatsink. A duty cycle of a pulse-width modulated power signal provided to the one or more thermoelectric devices is controlled in response to a target chamber temperature and real-time temperature measurements taken at the first location in the thermal chamber and at the second location on the internal heatsink.

In still another aspect, the invention features a liquid chromatography system comprising a solvent delivery system and a sample manager in fluidic communication with the solvent delivery system to obtain a mobile phase therefrom. The sample manager comprises a thermal chamber, an external heatsink disposed externally to the thermal chamber, an internal heatsink disposed within the thermal chamber, and one or more thermoelectric devices thermally coupled to the external and internal heatsinks to transfer heat therebetween in response to a pulse-width modulated power signal. A first temperature sensor disposed within the thermal chamber continuously measures a chamber temperature. A second temperature sensor coupled to the internal heatsink within the thermal chamber continuously measures temperature at the internal heatsink. A feedback control system controls a duty cycle of the pulse-width modulated power signal in response to a target chamber temperature and real-time temperature measurements produced by the first and second temperature sensors.

BRIEF DESCRIPTION OF THE DRAWINGS

The above and further advantages of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

DETAILED DESCRIPTION

Sample managers of liquid chromatography systems, as described herein, implement a thermal system that uses a dual-loop feedback control system to control temperature within the thermal chamber. The thermal system includes a heater/cooler (H/C) engine having one or more thermoelectric devices thermally coupled to two heatsinks, one external to the thermal chamber, and the other internal to the thermal chamber. The thermoelectric devices transfer heat between the heatsinks in response to a pulse-width modulated power signal. Typically, chromatography runs use the H/C engine to cool the thermal chamber, although the principles described herein apply also to those applications in which the thermal system configures the H/C engine to heat the thermal chamber.

The dual-loop feedback control system controls (i.e., modulates) the duty cycle of this pulse-width modulated power signal in response to a target chamber temperature and to real-time temperature measurements taken at the internal heatsink and at a second location within the thermal chamber. By controlling the temperature of the thermal chamber and the internal heatsink, the thermal system can avoid or detect problematic conditions, such as icing on the internal heatsink.

In addition, when a door to the thermal chamber opens, the thermal system switches to controlling only the temperature of the internal heatsink (by suspending control of the thermal chamber temperature). In effect, the dual-loop feedback control system temporarily changes to single-loop feedback control. This change in operation allows faster temperature recovery from open-door events and prevents heatsink icing when the door is open.

Figure 1:
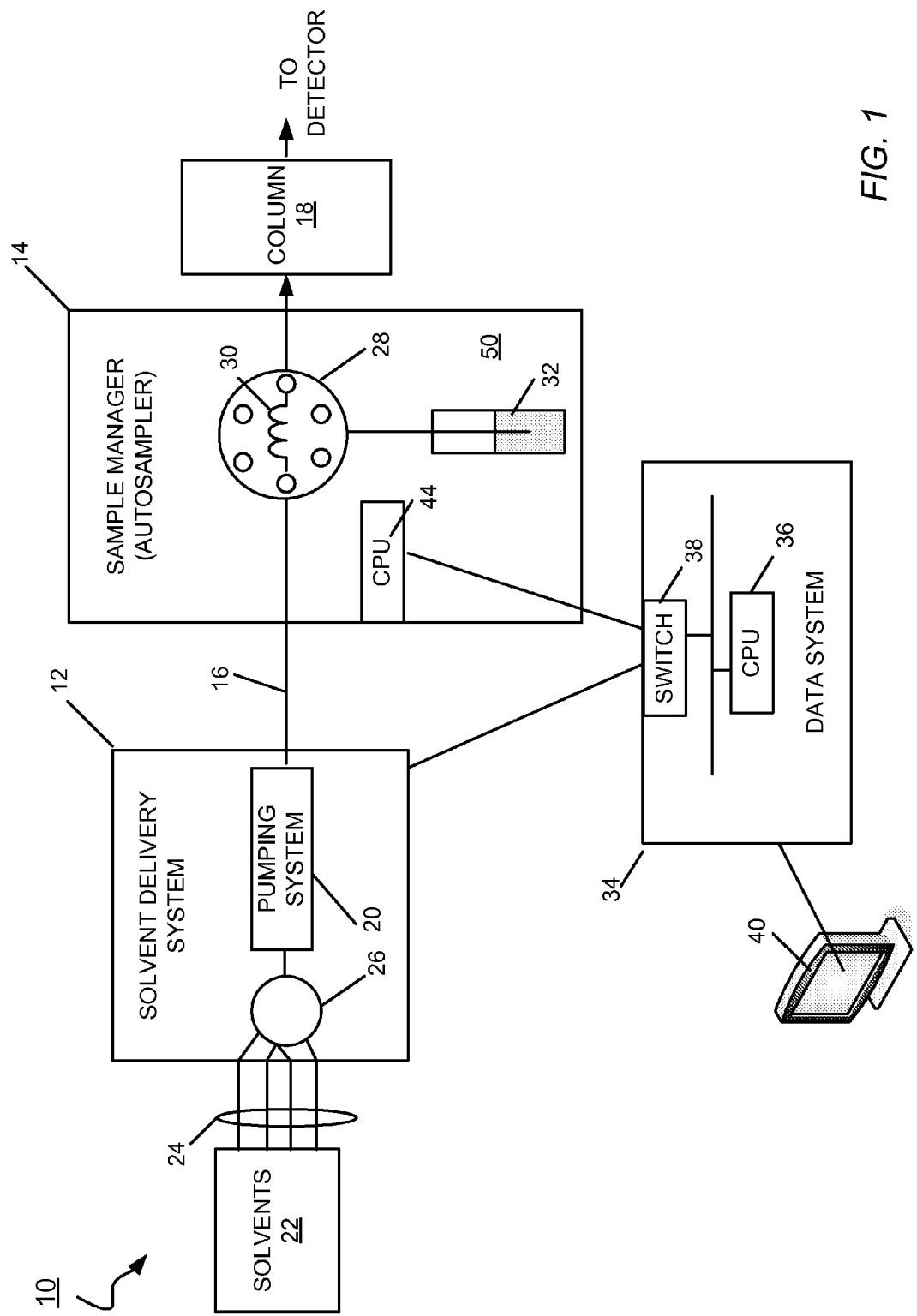
FIG. 1 is a functional block diagram of an embodiment of a liquid chromatography system including a sample manager.

FIG. 1 shows an embodiment of a liquid chromatography system 10 for separating a mixture into its constituents. The liquid chromatography system 10 includes a solvent delivery system 12 in fluidic communication with a sample manager 14 (also called an injector or an autosampler) through tubing 16. The sample manager 14 is in fluidic communication with a chromatographic column 18. A detector (not shown), for example, a mass spectrometer, is in fluidic communication with the column 18 to receive the elution.

The solvent delivery system 12 includes a pumping system 20 in fluidic communication with solvent reservoirs 22 from which the pumping system 20 draws solvents (liquid) through tubing 24. In one embodiment, the pumping system 20 is embodied by a low-pressure mixing gradient pumping system having two pumps fluidically connected in series. In the low-pressure gradient pumping system, the mixing of solvents occurs before the pump, and the solvent delivery system 12 has a mixer 26 in fluidic communication with the solvent reservoirs 22 to receive various solvents in metered proportions. This mixing of solvents occurs in accordance with an intake profile, and produces a solvent (mobile phase) composition that varies over time (i.e., the gradient).

The pumping system 20 is in fluidic communication with the mixer 26 to draw a continuous flow of gradient therefrom for delivery to the sample manager 14. Examples of pumping systems that can be used to implement the pumping system 20 include, but are not limited to, the ACQUITY BSM (Binary Solvent Manger) and the ACQUITY QSM (Quaternary Solvent Manager), manufactured by Waters Corp. of Milford, Mass.

The sample manager 14 includes a thermal chamber 50 and an injector valve 28 having a sample loop 30. The sample manager 14 operates in one of two states: a load state and an injection state. In the load state, the position of the injector valve 28 is such that the sample manager 14 loads the sample 32 into the sample loop 30; in the injection state, the position of the injector valve 28 changes so that sample manager 14 introduces the sample in the sample loop 30 into the continuously flowing mobile phase from the solvent delivery system 12. The mobile phase thus carries the sample into the column 18.

The liquid chromatography system 10 further includes a data system 34 that is in signal communication with the solvent delivery system 12 and the sample manager 14. The data system 34 has a processor 36 and a switch 38 (e.g., an Ethernet switch) for handling signal communication between the solvent delivery system 12 and sample manager 14. Signal communication among the various systems and instruments can be electrical or optical, using wireless or wired transmission.

A host computing system 40 is in communication with the data system 34 by which a technician can download various parameters and profiles to the data system 34. The downloaded parameters include a desired setpoint chamber temperature at which to operate the thermal chamber 50 of the sample manager 14 during a chromatographic run. To attain this setpoint chamber temperature within the thermal chamber 50, a processor 44 runs software that implements a dual-loop feedback control system based on temperatures measured in the thermal chamber 50, as described in more detail below.

Figure 2:
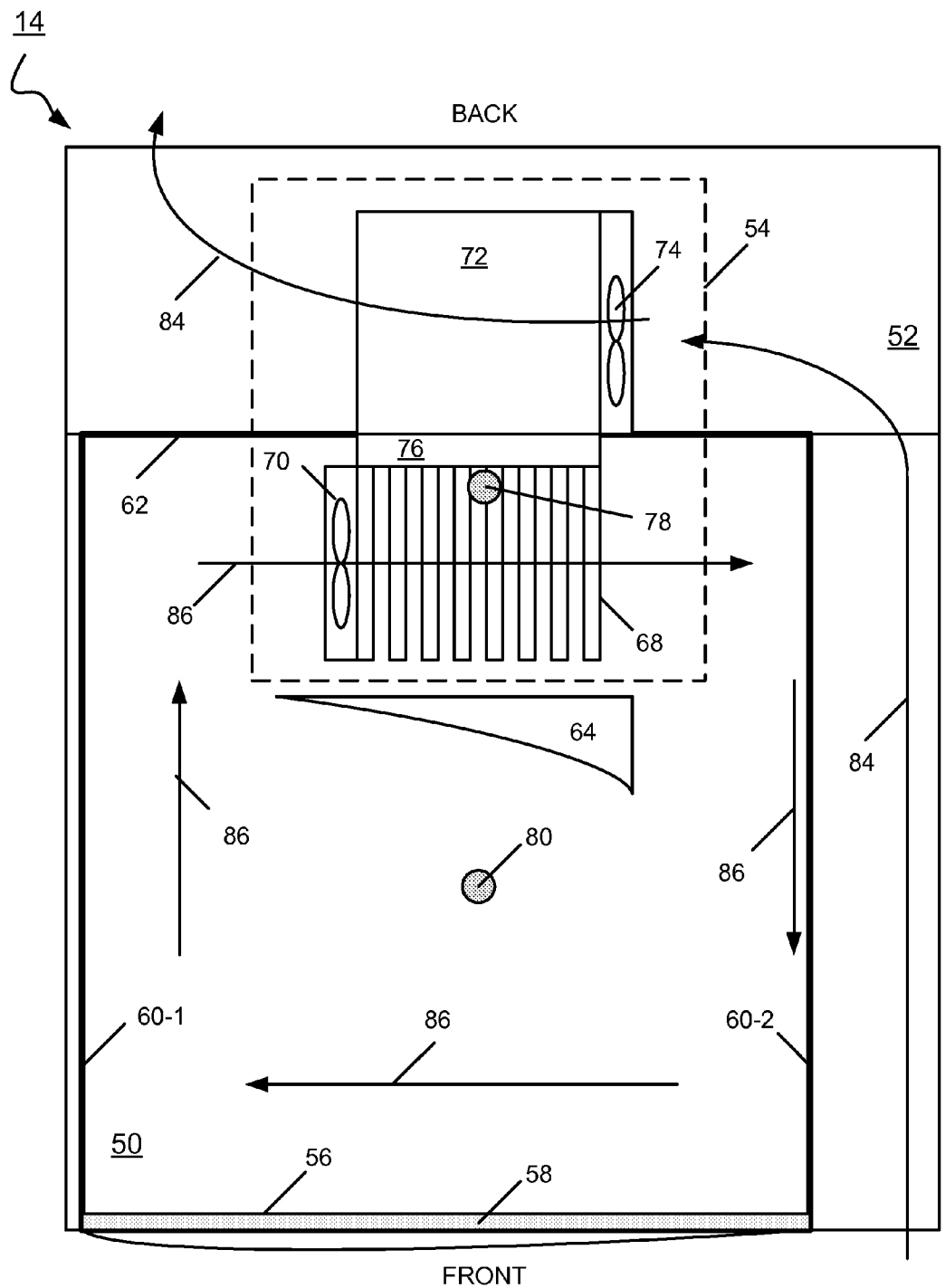
FIG. 2 is top view of an embodiment of a sample manager, including a thermal chamber and a heater/cooler engine for controlling temperature within the thermal chamber.

FIG. 2 shows a top view of an embodiment of the sample manager 14 including the thermal chamber 50, an exhaust chamber 52, and a heater/cooler (H/C) engine 54. The exhaust chamber 52 extends from the front side 56 of the sample manager 14, through foam ducting, and exits the back end of the sample manager 14.

The thermal chamber 50 has a front wall 56 with a door 58, side walls 60-1, 60-2, and a back wall 62. To thermally seal the thermal chamber, two-molded expanded polypropylene (EPP) foam components enclose the top and sides of the thermal chamber, while a datum plate, drip tray, and insulation layer enclose the bottom the thermal chamber. Adhesive-backing foam and plastic bulkheads may also be used. Within the thermal chamber is an interior wall 64 used to form an air duct along the back wall 62.

Mounted in the back wall 62 of the thermal chamber behind the interior wall 64, the H/C engine 54 is a primary active component in the thermal system. A portion of the H/C engine 54 resides within the thermal chamber and is referred to as the internal portion. Components of the internal portion are generally referred to herein as internal components. Another portion of the H/C engine 54 resides in the exhaust chamber 52 and is referred to as the external portion; the components of the external portion are generally referred to herein as external components.

One embodiment of the H/C engine 54 includes two thermoelectric chips (not shown), an internal heatsink 68 and an internal fan 70, an external heatsink 72 and an external fan 74, a separation plate 76, a heatsink temperature sensor 78, and a chamber temperature sensor 80. Embodiments of temperature sensors include, but are not limited to, thermistors. The internal heatsink 68 has a pocket (not shown) within which is disposed the heatsink temperature sensor 78. The heatsink temperature sensor 78 measures the temperature of the internal heatsink 68, referred to herein as the heatsink temperature. Disposed near a location in the thermal chamber where sample vials sit during a chromatographic run, the chamber temperature sensor 80 measures the chamber temperature. Other embodiments of the H/C engine 54 can have more than one temperature sensor within the chamber (e.g., multiple temperature sensors placed throughout the thermal chamber, instead of a single temperature sensor located near the sample vials).

Figure 3:
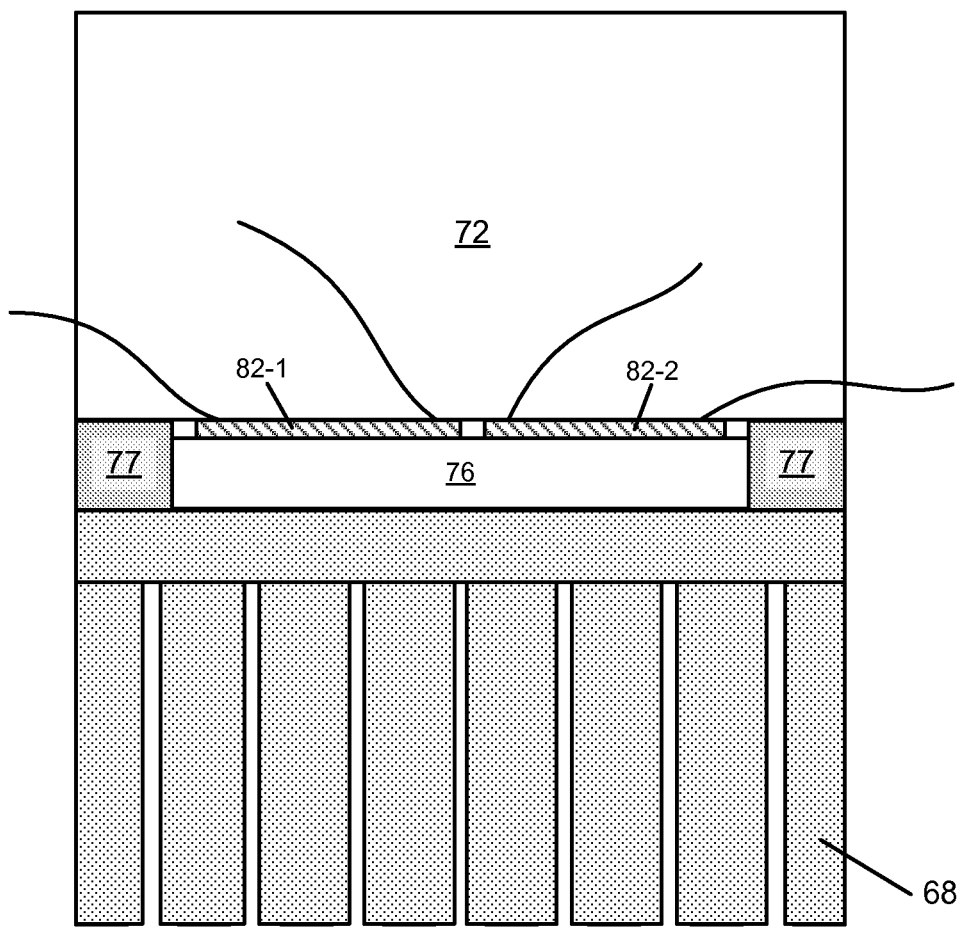
FIG. 3 is a side view of an embodiment of some components of the heater/cooler engine.

Referring to FIG. 3, the construction of the H/C engine 54 is in layers: the external heatsink 72, the two thermoelectric chips 82-1, 82-2 (generally, 82), the separation plate 76 (surrounded by insulation foam 77), and the internal heatsink 68. Bolts compress the layers, with spring washers maintaining the load. Other embodiments of the H/C engine 54 can have more or fewer than two thermoelectric chips.

The thermoelectric chips 82 are Peltier devices. Upon applying a DC voltage and a current source to the Peltier device, the Peltier device cools one side of the device and heats the other. The thermoelectric chips 82 operate as heat pumps to transfer heat from one heatsink to the other heatsink. The temperature difference produced by the thermoelectric chips 82 depends on several variables: material properties of the chips, the amount of heat being removed from the cold side, the average temperature of the chambers, and the drive current/voltage. Controlling the duty cycle of a pulse-width modulated power signal supplied to the thermoelectric chips 82 manipulates the amount of power delivered to the chips, affecting how strongly the thermoelectric chips 82 perform the heat transfer. For instance, increasing the duty cycle increases the drive of the thermoelectric chips 82. The relationship between duty cycle and performance of the thermoelectric chips 82 is not linear over the full range (0-100%) of possible duty cycles. For example, operating the chips 82 at 100% duty cycle does not achieve twice the performance as operating the chips at 50% duty cycle. A linearization look-up table that correlates duty cycles to heatsink temperatures can be used to ameliorate the non-linear behavior of the thermoelectric chips 82.

Returning to FIG. 2, the external fan 74 abutting the external heatsink 72 draws air in from the front of the sample manager 14 and through the external heatsink 72. The air exits the back of the sample manager 14. Arrows 84 represent the general direction of the airflow. The internal fan 70 abuts the internal heatsink 68 and circulates air within the thermal chamber 50 and through the internal heatsink 68 in the general direction represented by arrows 86. The transfer of heat within the thermal chamber 50 is achieved via convective airflow produced by the internal fan 70 through the internal heatsink of the H/C engine 54.

In one embodiment, by the operation of the thermoelectric chips, the H/C engine extracts heat from the thermal chamber 50 and drives the heat into the exhaust chamber 52, thereby cooling the thermal chamber. Alternatively, the thermoelectric chips can be configured to extract heat from the exhaust chamber and drive the heat into the thermal chamber, thereby heating the thermal chamber.

Figure 4:
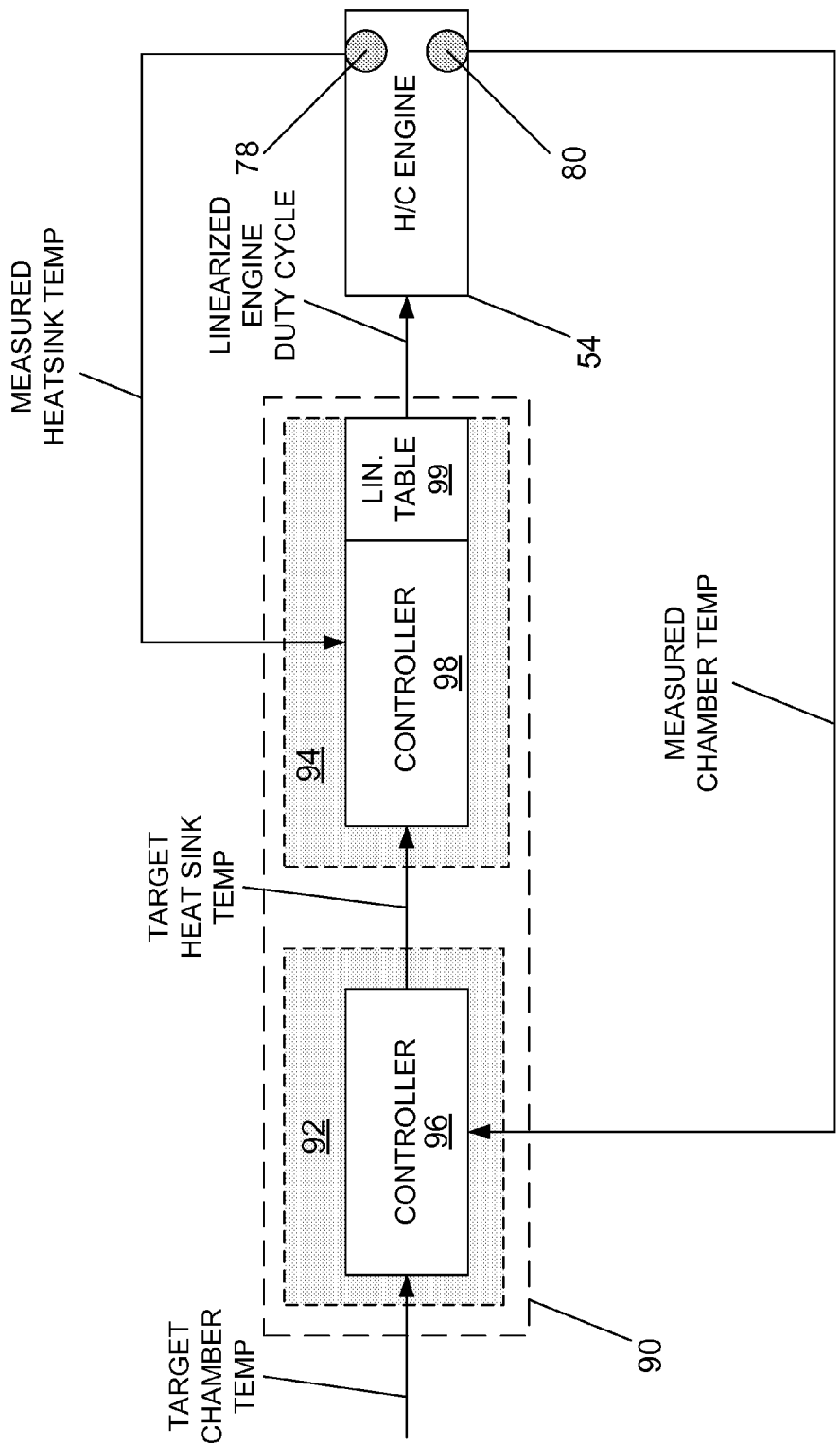
FIG. 4 is a functional block diagram of an embodiment of a dual-loop feedback control system used to control operation of the heater/cooler engine.

FIG. 4 shows an embodiment of a dual-loop feedback control system 90 used to control operation of the H/C engine 54. The dual-loop feedback control system 90 includes a first feedback control loop 92 in communication with a second feedback control loop 94. The second feedback control loop is in communication with the H/C engine 54, which includes the heatsink temperature sensor 78 and the chamber temperature sensor 80.

The first feedback control loop 92 (also referred to herein as the first loop) includes a controller 96. As input, the controller 96 receives the target chamber temperature from the data system 34 and the chamber temperature, as measured in real time by the chamber temperature sensor 80, and produces, as output, a target heatsink temperature. The controller 96 may clamp the target heatsink temperature to a predefined value if the processor 44 calculates a value that is less than a minimum threshold. The particular value of this predefined clamp value is selected such that if the H/C engine 54 succeeds in lowering the temperature to the clamp value, icing of the internal heatsink 68 will not occur. This clamp value can be below 0° C. (in one embodiment, the limit is –0.5° C.), because there can be a temperature difference between the heatsink temperature sensor and the heatsink surface temperature.

The second feedback control loop 94 (also referred to herein as the second loop) includes a controller 98. Provided as input to the controller 98 are the target heatsink temperature, received from the first loop 92, and the actual heatsink temperature, as measured in real-time by the heatsink temperature sensor 78. In response to this input, the controller 98 provides a linearized duty cycle to the H/C engine 54, to control the amount of power supplied to the H/C engine 54.

In one embodiment, each of the controllers 96, 98 are PID (proportional-integral-derivative) controllers that calculate an error value based on the difference between a desired setpoint and a measured parameter. Each controller operates to minimize the error in accordance with tuning parameters, such as proportional gain, integral gain, and derivative gain. For the controller 96 of the first loop 92, the setpoint is the target chamber temperature, and the measured parameter is the measured chamber temperature. For the controller 98 of the second loop 94, the setpoint is the target heatsink temperature from the first loop and the measured parameter is the measured heatsink temperature. The controller 98 of the second loop 94 accesses a linearization look-up table 99, which correlates duty cycle to heatsink temperature, and serves to linearize the behavior of the dual-loop feedback control system.

Figure 5:
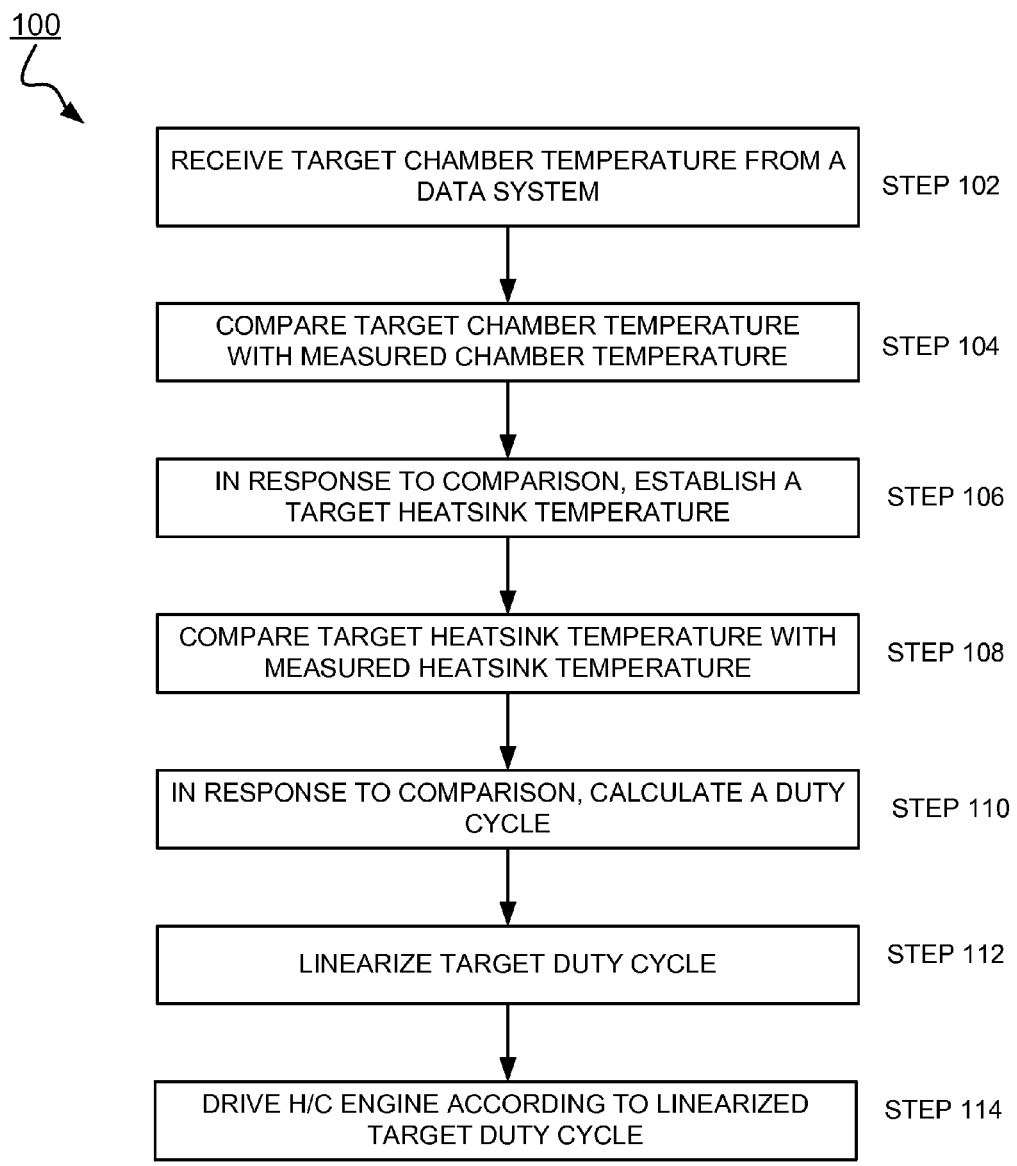
FIG. 5 is a flow diagram of an embodiment of a process for controlling temperature within the thermal chamber in accordance with the dual-loop feedback control system.

FIG. 5 shows an embodiment of a process 100 for controlling temperature within the thermal chamber 50 in accordance with the dual-loop feedback control system 90. The particular numbering of the steps of the process 100 is not intended to imply that the process occurs serially. For instance, during part of the process 100, the two feedback loops 96, 98 are operating continuously and concurrently based on real-time temperature measurements provided by the temperature sensors 78, 80. At step 102, a user of the sample manager 14, who is configuring the sample manager, for example, to perform a chromatographic run, establishes a target chamber temperature (also referred to as the setpoint). The controller 96 of the first feedback control loop 92 calculates (step 104) an error value based on the difference between the setpoint and a current chamber temperature as measured by the chamber temperature sensor 80. Based on this error value, the controller 96 calculates (step 106) a value for a target heatsink temperature, which passes to the controller 98 of the second feedback control loop 94. When the H/C engine is operating to cool the thermal chamber, the process 100 advantageously avoids icing of the internal heatsink by not allowing the controller 96 of the first feedback control loop 92 to produce a target heatsink temperature known to produce icing (i.e. not to be less than the clamp value).

The controller 98 of the second feedback control loop 94 calculates (step 108) an error value based on the difference between the target heatsink temperature (received from the first feedback control loop) and the current heatsink temperature as measured by the heatsink temperature sensor 78. From this error value, the controller 98 of the second feedback control loop 94 calculates (step 110) a value for a duty cycle designed to reduce the error. Using the linearization look-up table 99, the controller of the second feedback control loop acquires (step 112) a linearized value based on the calculated value, thereby acquiring a target duty cycle at which to drive the H/C engine 54. The pulse-width modulated power signal driving the H/C engine adjusts (step 114) accordingly to achieve the target duty cycle.

Thus, throughout a chromatographic run, the process 100 can be used to tune performance of the H/C engine dynamically (in real time) in order to approach and maintain a target chamber temperature. When used to cool the thermal chamber, the process 100 avoids icing on the internal heatsink 68 by ensuring the target heatsink temperature does not drop below a minimum limit. In one embodiment, opening the door of the sample manager interrupts the process 100.

Figure 6:
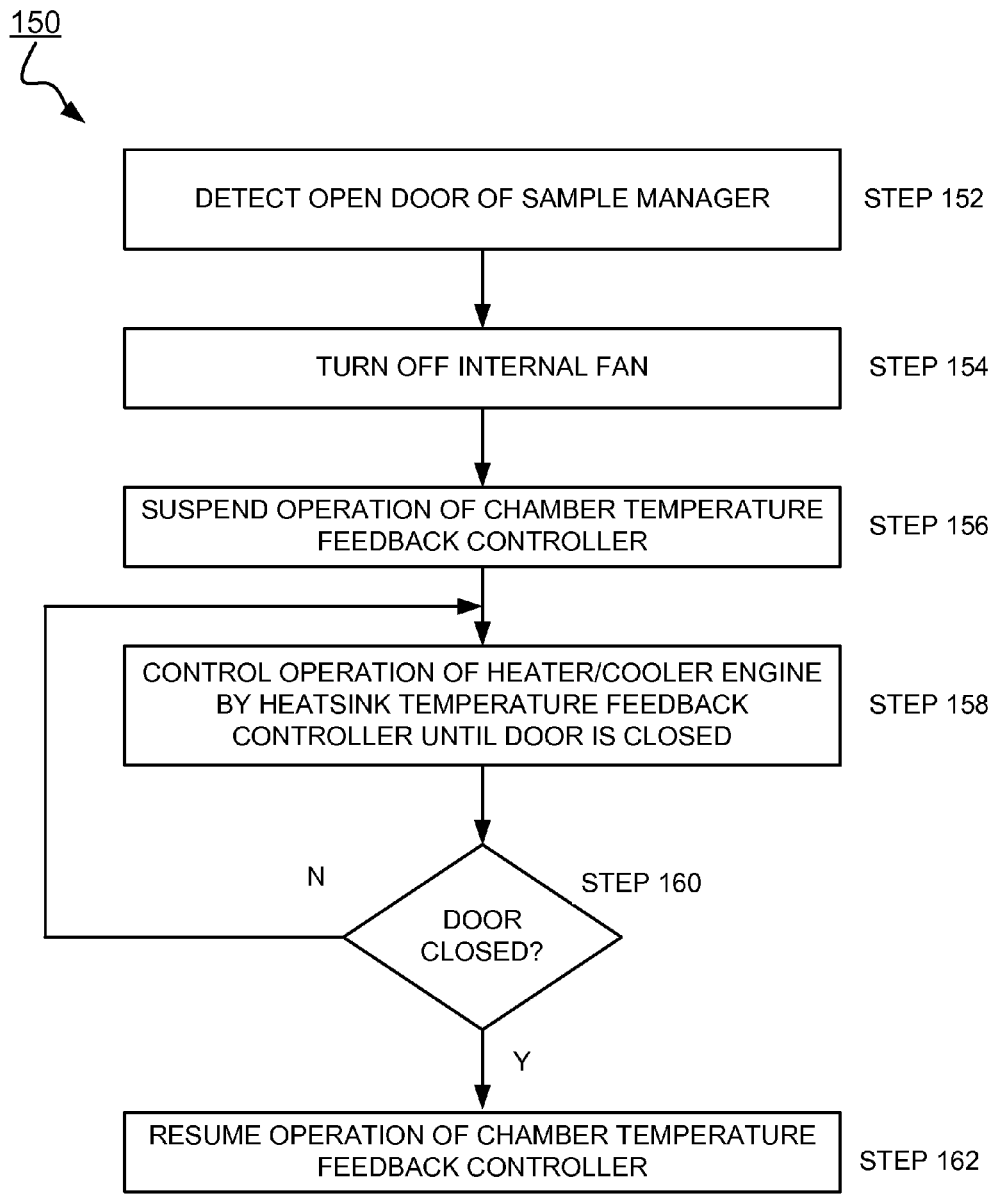
FIG. 6 is a flow diagram of an embodiment of a process for controlling operation of the heater/cooler engine when the door of the sample manager is opened.

FIG. 6 shows an embodiment of a process 150 for controlling operation of the H/C engine 54 when the door 58 of the sample manager 14 is opened. When the door of the sample manager opens, an "Open Door" signal is generated (step 152). In response to the Open Door signal, the internal fan 70 is turned off (step 154), to mitigate circulation of ambient air entering through the open door. Also in response to the Open Door signal, operation of the controller 96 of first loop 92 of the dual-loop feedback control system 90 is suspended (step 156), while the controller 98 of the second loop 94 continues (step 158) operation. Suspension of the first controller 96 entails holding its output (i.e., the target heatsink temperature) at the current value at the time of detecting the open door, and effectively removes the first loop 92 temporarily from the feedback control system while the door remains open, leaving the second loop 94 to control operation of the H/C engine.

When the door closes (step 160), the first loop 92 resumes (step 162) operation, with the controller 96 resuming its comparison of the target chamber temperature with the presently measured chamber temperature, and producing therefrom a target heatsink temperature, as described earlier.

While the invention has been shown and described with reference to specific preferred embodiments, it should be understood by those skilled in the art that various changes in form and detail may be made therein without departing from the spirit and scope of the invention as defined by the following claims.

What is claimed is:

1. An apparatus, comprising:
a thermal chamber;
an external heatsink disposed externally to the thermal chamber;
an internal heatsink disposed within the thermal chamber;
one or more thermoelectric devices thermally coupled to the external and internal heatsinks to transfer heat therebetween in response to a pulse-width modulated power signal;
a first temperature sensor disposed within the thermal chamber continuously measuring a chamber temperature;
a second temperature sensor coupled to the internal heatsink within the thermal chamber continuously measuring temperature at the internal heatsink; and
a feedback control system including a first controller in communication with the second temperature sensor as part of a first feedback control loop, the controller calculating the duty cycle of the pulse-width modulated power signal at which to operate the one or more thermoelectric devices in response to a target internal heatsink temperature and a real-time internal heatsink temperature measured by the second temperature sensor, wherein the feedback control system includes a second controller in communication with the first controller and the first temperature sensor as part of a second feedback loop, the second controller calculating the target internal heatsink temperature in response to a target chamber temperature and a real-time chamber temperature measured by the first temperature sensor, wherein the second controller passes the calculated target internal heatsink temperature to the first controller, and the first controller supplies the pulse-width modulated power signal to the one or more thermoelectric devices.

2. The apparatus of claim 1, further comprising a linearization table for correlating duty cycle values to internal heatsink temperature values, and wherein the controller accesses the linearization table when calculating the duty cycle of the pulse-width modulated power signal.

3. The apparatus of claim 1, wherein each controller is a PID (proportional-integral-derivative) controller.

4. The apparatus of claim 1, further comprising a door-open detector issuing an open-door signal when a door to the thermal chamber is opened, and wherein calculation of the target internal heatsink temperature by the second controller is suspended in response to the open-door signal and the target internal heatsink temperature is held at its last calculated value.

5. The apparatus of claim 4, wherein an internal fan is turned off in response to the open-door signal.

6. The apparatus of claim 1, wherein the second controller clamps the target internal heatsink temperature to a predefined value when the calculated target internal heatsink temperature is less than a minimum threshold.

7. The apparatus of claim 1, wherein the one or more thermoelectric devices are configured to cool the thermal chamber.

8. A method for controlling temperature in a thermal chamber of a liquid chromatography system, comprising:
transferring heat between an internal heatsink disposed within the thermal chamber and an external heatsink disposed externally to the thermal chamber using one or more thermoelectric devices thermally coupled to the external and internal heatsinks, in response to a pulse-width modulated power signal;
continually measuring temperature in real time at a first location within the thermal chamber with a first temperature sensor and at a second location coupled to the internal heatsink within the thermal chamber with a second temperature sensor; and
controlling a duty cycle of a pulse-width modulated power signal provided to the one or more thermoelectric devices with a feedback control system including a first controller in communication with the second temperature sensor as part of a first feedback control loop, the first controller calculating the duty cycle of the pulse-width modulated power signal at which to operate the one or more thermoelectric devices in response to a target internal heatsink temperature and a real-time internal heatsink temperature measured by the second temperature sensor, wherein the feedback control system includes a second controller in communication with the first controller and the first temperature sensor as part of a second feedback loop, the second controller calculating the target internal heatsink temperature in response to a target chamber temperature and a real-time chamber temperature measured by the first temperature sensor, wherein the second controller pass the calculated target internal heatsink temperature to the first controller, and the first controller supplies the pulse-width modulated power signal to the one or more thermoelectric devices.

9. The method of claim 8, further comprising:
correlating duty cycle values to heatsink temperatures in a linearization table; and
accessing the linearization table when calculating the duty cycle.

10. The method of claim 8 further comprising
issuing an open-door signal when a door to the thermal chamber is opened;
holding the target heatsink temperature at its last calculated value; and
suspending subsequent calculation of the target heatsink temperature while the door remains open.

11. The method of claim 10, further comprising ceasing to circulate air within the thermal chamber through the internal heatsink in response to the open-door signal.

12. The method of claim 8, further comprising clamping the target heatsink temperature to a predefined value when the calculated target heatsink temperature is less than a minimum threshold.

13. The method of claim 8, further comprising configuring the one or more thermoelectric devices to cool the thermal chamber.

14. A liquid chromatography system, comprising:
a solvent delivery system; and
a sample manager in fluidic communication with the solvent delivery system to obtain a mobile phase therefrom, the sample manager comprising:
a thermal chamber;
an external heatsink disposed externally to the thermal chamber;
an internal heatsink disposed within the thermal chamber;
one or more thermoelectric devices thermally coupled to the external and internal heatsinks to transfer heat therebetween in response to a pulse-width modulated power signal;
a first temperature sensor disposed within the thermal chamber continuously measuring a chamber temperature;
a second temperature sensor coupled to the internal heatsink within the thermal chamber continuously measuring temperature at the internal heatsink;
and a feedback control system including a first controller in communication with the second temperature sensor as part of a first feedback control loop, the first controller calculating a duty cycle of the pulse-width modulated power signal at which to operate the one or more thermoelectric devices in response to a target internal heatsink temperature and a real-time internal heatsink temperature measured by the second temperature sensor, wherein the feedback control system includes a second controller in communication with the first controller and the first temperature sensor as part of a second feedback loop, the second controller calculating the target internal heatsink temperature in response to a target chamber temperature and a real-time chamber temperature measured by the first temperature sensor, wherein the second controller passes the calculated target internal heatsink temperature to the first controller, and the first controller supplies the pulse-width modulated power signal to the one or more thermoelectric devices.

15. The liquid chromatography system of claim 14, further comprising a linearization table for correlating duty cycle values to heatsink temperatures, and wherein the controller of the second feedback control loop accesses the linearization table when calculating the duty cycle.

16. The liquid chromatography system of claim 14, further comprising a door-open detector issuing an open-door signal when a door to the sample manager is opened, and wherein operation of the first feedback control loop is suspended in response to the open-door signal and the target heatsink temperature is held at its last calculated value.

17. The liquid chromatography system of claim 14, wherein the controller of the first feedback control loop clamps the target heatsink temperature to a predefined value when the calculated target heatsink temperature is less than a minimum threshold.

\* \* \* \* \*

UNITED STATES PATENT AND TRADEMARK OFFICE
CERTIFICATE OF CORRECTION

PATENT NO. : 9,091,467 B2 Page 1 of 1
APPLICATION NO. : 13/519776
DATED : July 28, 2015
INVENTOR(S) : Joshua A. Shreve and Steven J. Ciavarini It is certified that error appears in the above-identified patent and that said Letters Patent is hereby corrected as shown below:

In the claims

Column 8, Claim 8:, line 58, after the words "sensor, wherein the second controller" replace the word "pass" with "passes".

Signed and Sealed this
Twelfth Day of January, 2016

Michelle K. Lee
*Director of the United States Patent and Trademark Office*